United States Patent [19]

Yamasawa

[11] Patent Number: 4,850,369
[45] Date of Patent: Jul. 25, 1989

[54] CUFF FOR BLOOD PRESSURE MEASURING APPARATUS

[75] Inventor: Tsutomu Yamasawa, Takatsuki, Japan

[73] Assignee: Omron Tateisi Electronics Co., Kyoto, Japan

[21] Appl. No.: 105,358

[22] Filed: Oct. 7, 1987

Related U.S. Application Data

[63] Continuation-in-part of Ser. No. 933,892, Nov. 24, 1986, abandoned, which is a continuation-in-part of Ser. No. 850,819, Apr. 11, 1986, abandoned.

[30] Foreign Application Priority Data

| Apr. 12, 1985 | [JP] | Japan | 60-78651 |
| Apr. 12, 1985 | [JP] | Japan | 60-78653 |
| Apr. 12, 1985 | [JP] | Japan | 60-78655 |
| Apr. 12, 1985 | [JP] | Japan | 60-78657 |
| Apr. 12, 1985 | [JP] | Japan | 60-78658 |
| Apr. 15, 1985 | [JP] | Japan | 60-81025 |
| Nov. 25, 1985 | [JP] | Japan | 60-181640 |

[51] Int. Cl.$^4$ .............................................. A61B 5/02
[52] U.S. Cl. .................................................... 178/686
[58] Field of Search ................................ 128/680-683, 128/686-690, 664-667, 662

[56] References Cited

U.S. PATENT DOCUMENTS

| 3,482,565 | 12/1969 | Gowen | 128/667 |
| 3,908,636 | 2/1974 | Page | 128/666 |
| 4,030,483 | 6/1977 | Stevens | 128/666 |
| 4,063,551 | 12/1977 | Sweeney | 128/666 |
| 4,129,124 | 12/1978 | Thalman | 128/666 |
| 4,163,447 | 8/1979 | Orr | 128/666 |

FOREIGN PATENT DOCUMENTS

| 2842337 | 4/1979 | Fed. Rep. of Germany | 128/686 |
| 3109822 | 9/1982 | Fed. Rep. of Germany | 128/686 |

OTHER PUBLICATIONS

Hammer, W. E. et al, "Blood Pressure Finger Cuff", IBM Tech. Discl. Bulletin, vol. 8, #4, Sep. 1965.

*Primary Examiner*—Francis Jaworski
*Attorney, Agent, or Firm*—Wegner & Bretschneider

[57] ABSTRACT

A cuff for blood pressure measuring apparatus, which is made of flexible material, includes an inner surface and outer surface. The inner surface defines a cylindrical space for a finger to be inserted thereinto, while the outer surface together with the inner surface defines a fluid chamber for applying pressure to the finger. A light-emitting element for emitting light at an artery of the finger and a light-sensitive element for receiving the reflected light from said artery are mounted on the inner surface adjacent to each other. A plurality of elements are provided at least either for the light-emitting element or for the light-sensitive element, thereby expanding the detection range of the arterial pulse wave in the finger. The cuff is also provided with a device for triggering or halting air into or from the cuff when desired and for ensuring that air is exited from the cuff.

9 Claims, 6 Drawing Sheets

CUFF FOR BLOOD PRESSURE MEASURING APPARATUS

REFERENCE TO RELATED APPLICATIONS

This application is a continuation-in-part of application Ser. No. 933,892, filed Nov. 24, 1986, now abandoned, which is a continuation-in-part of application Ser. No. 850,819, filed Apr. 11, 1986 now abandoned, the disclosure of which was incorporated by reference in application Ser. No. 933,892 as if fully set forth therein. The disclosures of applications Ser. Nos. 933,892 and 850,819 are incorporated by reference into this application as if fully set forth therein.

BACKGROUND AND SUMMARY OF THE INVENTION

This invention relates to a cuff for blood pressure measuring devices, and more particularly to a cuff which is adapted to the detection of a pulse wave in a person's finger, rather than in an arm.

A cuff has been disclosed in the article "New oscillometric method for indirect measurement of systolic and mean arterial pressure in the human finger", Med. & Biol. Eng. & Comp., May 1982, pp. 314–318, which has disposed therein a light-emitting element and light-sensitive element opposing each other, in which the light emitted from the light-emitting element is received by the light-sensitive element after passing through the artery of a finger, thereby detecting a pulse wave. In this detector however, since the light must pass the distance corresponding to the width of the finger, it is difficult to achieve the sensitivity required for highly accurate measurement.

For this reason, the inventor of this application and their colleagues employed by their common assignee have devised an improved cuff, applications to which were filed on Apr. 11, 1986, assigned U.S. Ser. No. 850,819 and Nov. 24, 1986, assigned U.S. Ser. No. 933,892. In FIGS. 1(a) and 1(b) of prior application Ser. No. 850,819, a single light-emitting element 3 and a single light-sensitive element 4 are shown as mounted adjacent to each other on the inner surface of the cuff 2. The light emitted from the light emitting element 3 is reflected from the artery 6 of a finger 5 and received by the light-sensitive element 4. In this application the invention of prior application Ser. No. 850,819 is shown in FIG. 5, which is described further below.

In the cuff disclosed in Ser. No. 850,819, a light-path can be shortened because the light-emitting element and lightsensitive element are disposed close to the artery of the finger, so that the level of a pulse wave signal can be multiplied to improve the sensitivity. However, since the prior cuff has only a single pair of light-emitting and light-sensitive elements disposed close to each other, the detectable range of a pulse wave is limited as shown by the broken line in FIG. 5 of this application. Accordingly, a desired pulse wave as shown in FIG. 6 of this application cannot be detected unless the finger is inserted into a cylindrical space such that the artery 64 of the finger is covered by the limited detection range.

In addition, the location of the finger artery differs from person to person, which makes it difficult to guide the finger into an appropriate position for accurate measurement. Thus, as shown in FIG. 7 of this application, the finger is often inserted with its artery not covered by the detectable range. In this condition, the peak value of the detected pulse wave cannot be clearly identified as shown in FIG. 8 of this application, thus making it difficult to measure an accurate blood pressure.

Moreover, it is desirable to provide a means for triggering air into the cuff when desired. In order to avoid overpressurization of the cuff when not in use, a means is also provided for ensuring that air is exited from the cuff. Further, a means is provided for halting the pressurization of the cuff when desired.

It is, accordingly, an object of this invention to provide a cuff for blood pressure measuring apparatus which overcomes the above-mentioned disadvantages.

It is another object to provide a cuff for blood pressure measuring apparatus which is capable of detecting an appropriate pulse wave for accurate measurement.

It is still another object to provide a cuff for blood pressure measuring apparatus whose pulse wave detection range is expanded to cover finger arteries which are differently located from person to person.

According to one aspect of this invention, there is provided a cuff for a blood pressure measuring apparatus, which is made of flexible material, comprising an inner surface defining a cylindrical space for a finger to be inserted thereinto, an outer surface together with the inner surface defining a fluid chamber therebetween which applies pressure to the finger, a light-emitting element mounted on the inner surface for emitting light at the artery of the finger, a light-sensitive element mounted on the inner surface adjacent to the light-emitting element for receiving the reflected light from the artery, wherein a plurality of elements are provided at least either for the light-emitting element or for the light-sensitive element. That is, if one light-emitting element is employed, then at least two light-sensitive elements are used, and vice versa. The invention also incudes the use of two or more of each of the light-emitting and light-sensitive elements.

Further, the invention includes a microswitch operably connected to an air pump suitable for being triggered when air supply is required in the air chamber of the cuff. In order to trigger the microswitch, an actuator lever inside the cuff is provided for activating the microswitch when the finger is properly seated thereon. The actuator lever is provided in such a way that when the finger is not seated thereon, the actuator lever permits air to exit from the cuff to avoid undesired overpressurization of the cuff. The invention also includes a light emitting device (LED) and light receiving device (LRD) inside the cuff in order to control the air intake of the cuff when desired.

Other objects and numerous advantages of the cuff for blood pressure apparatus according to this invention will become apparent from the following description when considered in conjunction with the accompanying drawings.

DETAILED DESCRIPTION OF THE INVENTION

Figure 1:
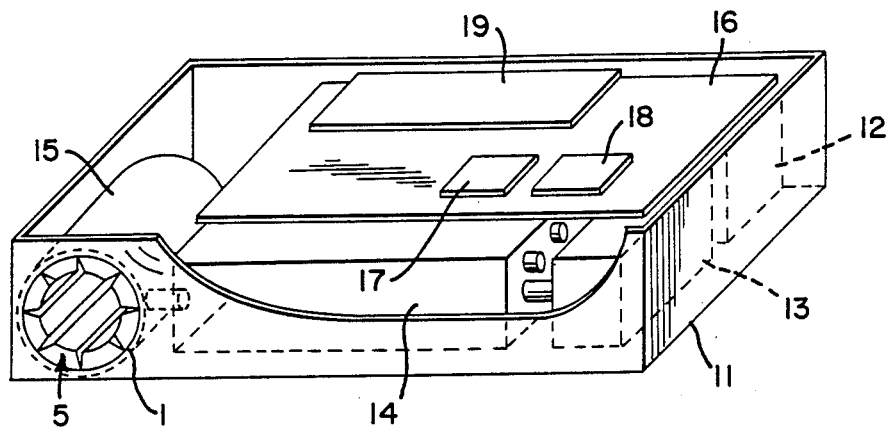
FIG. 1 is a perspective view showing the appearance of the blood pressure measuring apparatus including a cuff of this invention.

FIG. 1 shows a partially broken away perspective view of a blood pressure measuring apparatus including a cuff of this invention. A main body casing 11 accommodates a battery unit 12, an air pump 13, an air buffer 14, and a cuff unit 15. Further, a circuit board 16 extends over the top surfaces of the air buffer 14, the battery unit 12, and the air pump 13. A power switch 17, a start switch 18 and a liquid crystal display unit 19 are attached to the top surface of the circuit board 16 and appropriate electronic connections are made therebetween although not shown in the drawing. Also, a MPU, pressure sensor, and other electronic components are mounted on the lower surface of the circuit board 16, which are not shown here. The cuff unit 15 includes a tubular member 1 and a cuff 5 housed in the tubular member 1.

Figure 2:
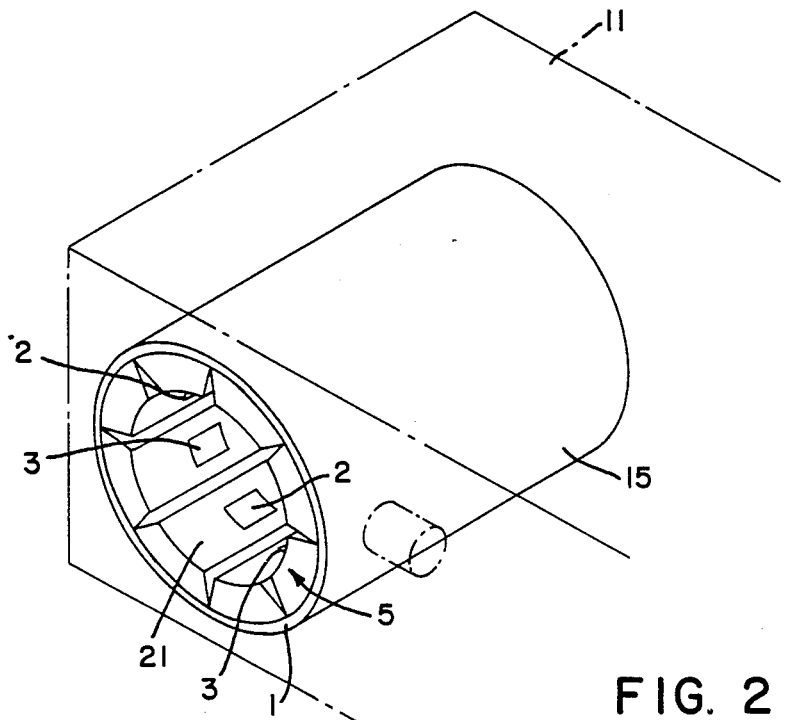
FIG. 2 is a partially enlarged perspective view showing the cuff of FIG. 1.

FIG. 2 shows an embodiment of the cuff 5 for the blood pressure measuring apparatus of this invention. The cuff 5 is provided with a pulse wave sensor which is composed of a plurality of light-emitting elements 2 and light-sensitive elements 3. These elements are mounted in an indented portion 24 formed on an inner surface 102 of cuff 5, as shown in FIG. 3.

Figure 3:
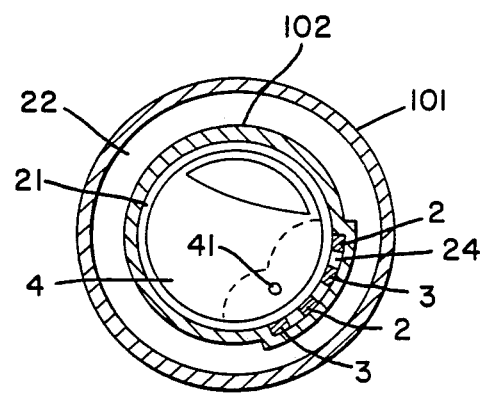
FIG. 3 is a sectional view of the cuff of FIG. 1.

During the measuring operation, the cuff 5 applies pressure to the finger 4 through the pumping up of an air chamber 22 which is formed between an inner surface 102 and outer surface 101 of cuff 5, after a finger 4 is inserted into a cylindrical space 21 defined by the inner surface 102 as shown in FIG. 3. Under this condition, light-emitting elements 2 emit light at the artery 41, the reflected light from which is received by light-sensitive elements 3, thereby detecting a pulse wave which changes during the pressurizing or depressurizing process. The value of blood pressure is determined on the basis of the detected pulse wave and the pressure data of the cuff 5, and is visually displayed.

In this embodiment, light-emitting elements 2 and lightsensitive elements 3 are alternately disposed such that the artery of the finger is approximately centered with respect to such elements as long as the finger is appropriately inserted into the cylindrical space 21.

Figure 4:
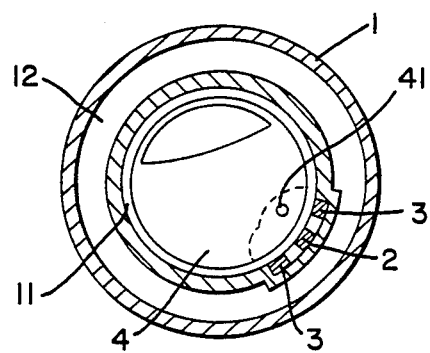
FIG. 4 is a sectional view of another embodiment of the cuff of FIG. 1.
Figure 5:
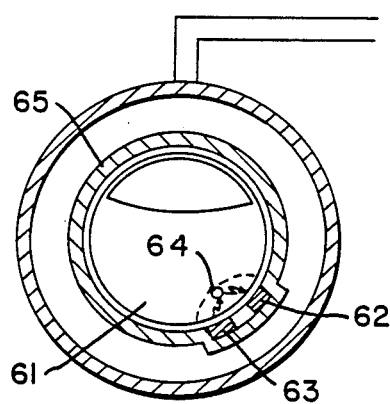
FIG. 5 is a sectional view illustrating a cuff having a single light-emitting and light-sensitive element pair.
Figure 6:
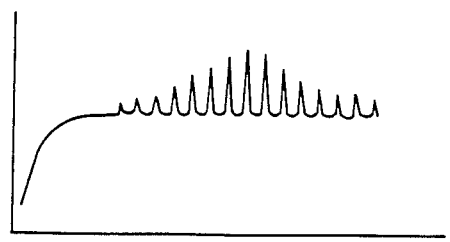
FIG. 6 is a timing waveform of an appropriately detected pulse wave.
Figure 7:
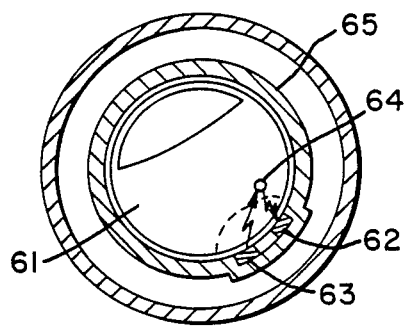
FIG. 7 is a sectional view illustrating a cuff of FIG. 5 in which a finger is inserted with its artery is not covered by the pulse wave detection range.
Figure 8:
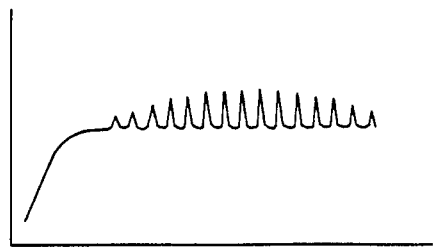
FIG. 8 is a timing waveform of a detected pulse wave in which the finger is inserted as shown in FIG. 7.

FIG. 4 shows another embodiment of this invention in which a single light-emitting element 1 is interposed between a pair of light-sensitive elements 3.

These cuffs as shown in FIGS. 3 and 4 can greatly expand the detectable pulse wave ranges, which are shown by the broken lines, in comparison with those that have only a single pair of light-emitting and light-sensitive elements. Accordingly, the artery pulse wave can be securely detected even where the finger is not inserted into the cylindrical space 21 at the most appropriate angle.

Figure 9:
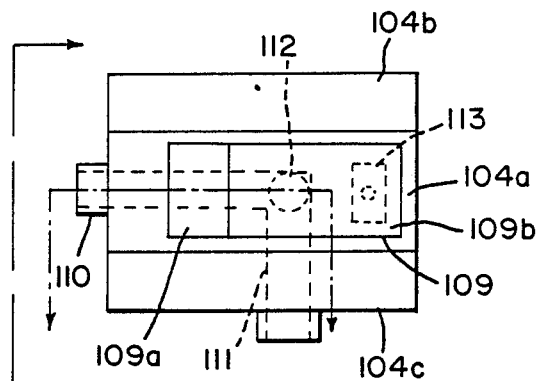
FIG. 9 is a top elevational view of a cuff unit of this invention having an actuator lever employed therein.
Figure 10:
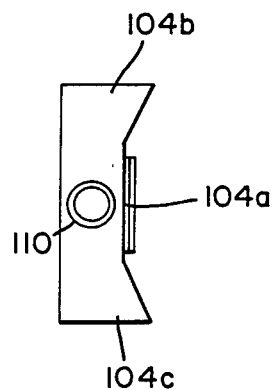
FIG. 10 is a front elevational view taken in the direction of arrows A—A of the cuff unit showing a finger receptacle inside the cuff unit having the actuator lever employed thereon.

As shown in FIG. 9, an actuator lever 109 can be employed inside the cuff unit 15 shown in FIGS. 1 and 2. The actuator lever 109 has a fixed portion 109a mounted on a finger receptacle 104 and a working portion 109b located above a button 113a of a microswitch 113. As further shown in FIG. 9, air outlet 110 extends from an air duct 111 having an air escape hole 112. The finger receptacle 104 has a central portion 104a for directly accommodating the actuator lever 109. The finger receptacle 104 further has sloping side portions 104b, 104c for directing the finger to the actuator lever 109 during finger insertion into the cuff unit 15.

Figure 11:
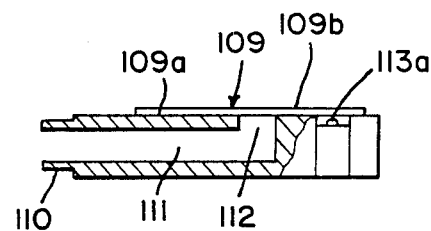
FIG. 11 is a cross-sectional view taken in the direction of arrows B—B shown in FIG. 9 illustrating the actuator lever in its activated state.
Figure 12:
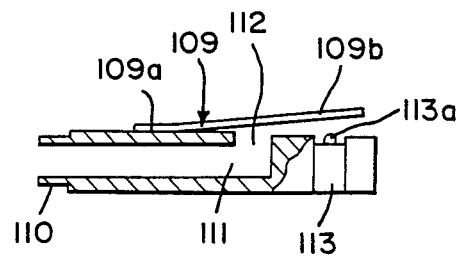
FIG. 12 is a cross-sectional view taken in the direction of arrows A—A shown in FIG. 9 illustrating the actuator lever in its deactivated state.

As better illustrated in FIGS. 11 and 12, the working portion 109b of the actuator lever 109 extends above the microswitch button 113a when deactivated. Typically, when a finger is inserted in the cuff unit 15 and properly seated on the actuator lever 109 so that the working portion 109b pushes down on the microswitch button 113a, as shown in FIG. 11, the microswitch 113 is activated to provide signals for operating the air pump 13 (see FIG. 1). When the actuator lever 109 is in the deactivated state, shown in FIG. 12, the air escape hole 112 is unblocked thereby allowing air to exit from the air duct 111. In other words, the cuff unit 15 is not pressurized when the escape hole 112 is unblocked, thus providing a safety feature of preventing unwanted overpressurization of the cuff unit even when air is being supplied to the cuff unit 15 with the microswitch 113 having been deactivated.

By providing an escape hole 112 through the air duct 111, the operation of the cuff unit 15 need not be dependent upon the microswitch 113 for deactivating the air pump 13. In other words, even if a start switch 188, as in FIG. 1, instead of the microswitch 113, is provided for activating or deactivating the air pump 13, the removal of the finger will allow air to escape through the escape hole 112, thus preventing undesired overpressurization of the cuff unit 15. Accordingly, a double safety feature is provided for preventing the unwanted overpressurization of the cuff unit 15 by allowing air to exit through the escape hole 112 or deactivating the air pump 13 by way of microswitch 113 when the cuff unit 15 is not in use.

Figure 13:
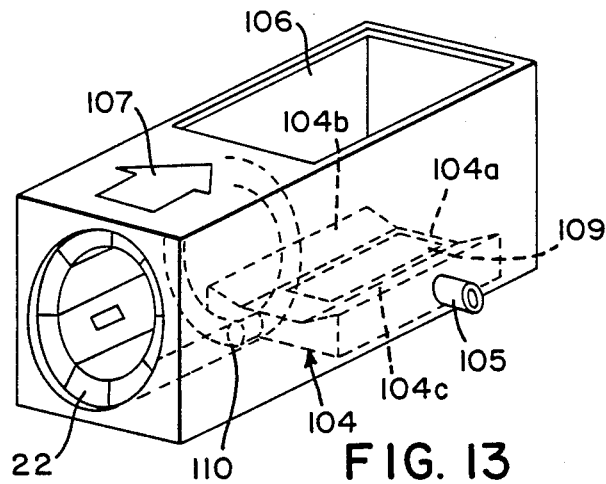
FIG. 13 is a perspective view of the cuff unit of this invention illustrating the actuator lever employed on a finger receptacle below a transparent window.
Figure 14:
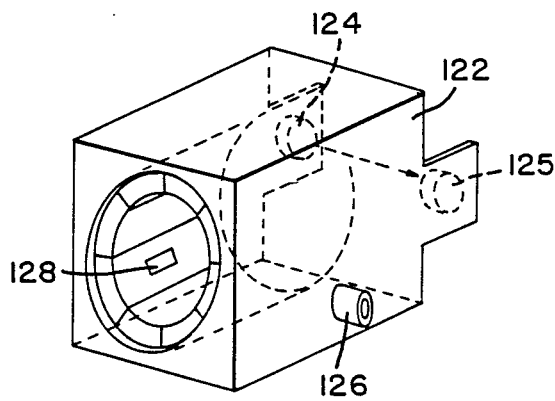
FIG. 14 is a perspective view of another embodiment of the cuff unit of the instant invention having a light emitting device in combination with a light receiving device for activating or deactivating the pressurization of the cuff.

In order to have a better view of the position of the finger inside the cuff unit 15, a transparent window 106 is provided in the upper portion of the cuff unit 15, as shown in FIG. 13. As also shown in FIG. 13, the air outlet 10 is accommodated within the air chamber 22 (see, e.g., FIG. 3). On the upper portion of the cuff unit 15, a sign or arrow 107 can be provided for the direction of finger insertion.

In another embodiment of this invention, a light emitting device (LED) 124 in combination with a light receiving device (LRD) 125, instead of the previously discussed actuator lever 109 or microswitch 113, are provided in a cuff unit 122 having at least one pulse wave sensor 128 and an air inlet 126, for activating or deactivating the pressurization of the cuff unit. The LED-LRD 124, 125 combination triggers the start up of the air pumo 13 when the finger blocks off the light passing between the LED 124 and LRD 125.

It should be understood that the above description is merely illustrative of this invention and that many changes and modifications may be made without departing from the scope of the appended claims.

What is claimed is:

1. A cuff for a blood pressure measuring apparatus, which is made of flexible material and has an inner surface defining a cylindrical space for a finger to be inserted thereinto and an outer surface together with said inner surface defining a fluid chamber therebetween which applies pressure to the finger, comprising:
    a plurality of light-emitting elements mounted on said inner surface for emitting light at an artery of the finger; and
    a plurality of light-sensitive elements mounted on said inner surface adjacent to said light-emitting elements, for receiving the reflected light from the artery,
    wherein said plurality of light-emitting elements and said plurality of light-sensitive elements are alternately disposed on said inner surface.

2. The cuff for blood pressure measuring apparatus according to claim 1, further comprising:
    a fluid pump actuator for releasing fluid into the fluid chamber; and
    a finger receptacle inside the cuff for accommodating the finger.

3. The cuff for blood measuring apparatus according to claim 2, further comprising a fluid duct having a fluid escape aperture passing therethrough into the cylindrical space.

4. The cuff for blood pressure measuring apparatus according to claim 2, wherein the fluid pump actuator comprises an actuator lever mounted on the finger receptacle and a microswitch operably coupled to a fluid pump.

5. The cuff for blood pressure measuring apparatus according to claim 4, wherein the actuator has a fixed portion mounted on the finger receptacle and a working portion extending above the microswitch suitable for receiving the finger and activating the microswitch.

6. The cuff for blood pressure measuring apparatus according to claim 2, wherein the finger receptacle has a central portion for accommodating the fluid pump actuator and sloped side portions for directing the finger being inserted onto the fluid pump actuator.

7. The cuff for blood measuring apparatus according to claim 3, wherein the fluid escape aperture permits escape of fluid into the cylindrical space when the fluid pump actuator is deactivated.

8. The cuff for blood measuring apparatus according to claim 6, further comprising a fluid duct having a fluid escape aperture passing therethrough into said cylindrical space, wherein said fluid escape aperture permits escape of fluid into said cylindrical space while said actuator lever is deactivated even if the fluid pump still pressurizes the cuff.

9. A cuff for a blood pressure measuring apparatus, which is made of flexible material and has an inner surface defining a cylindrical space for a finger to be inserted thereinto and an outer surface together with said inner surface defining a fluid chamber therebetween which applies pressure to the finger, comprising:
    at least one light-emitting element mounted on said inner surface for emitting light at an artery of the finger;
    at least one light-sensitive element mounted on said inner surface adjacent to said light-emitting element, for receiving the reflected light from the artery, wherein a plurality of elements is provided at least for the light-emitting element or for the light-sensitive element;
    a fluid pump actuator for releasing fluid into said fluid chamber; and
    a finger receptacle inside said cuff for accommodating the finger;
    wherein the fluid pump actuator comprises at least one light emitting device for transmitting light into at least one light receiving device for triggering a fluid pump to release fluid into the cylindrical space when the finger blocks off the transmitted light.

* * * * *